(12) United States Patent
Gurjar et al.

(10) Patent No.: US 8,952,155 B2
(45) Date of Patent: Feb. 10, 2015

(54) RILPIVIRINE PROCESS

(75) Inventors: Mukund Keshav Gurjar, Pune (IN); Golakchandra Sudarshan Maikap, Pune (IN); Shashikant Gangaram Joshi, Pune (IN); Sachin Aravind Badhe, Pune (IN); Samit Satish Mehta, Pune (IN)

(73) Assignee: Emcure Pharmaceuticals Limited, Pune (IN)

( * ) Notice: Subject to any disclaimer, the term of this patent is extended or adjusted under 35 U.S.C. 154(b) by 0 days.

(21) Appl. No.: 13/880,843

(22) PCT Filed: Apr. 9, 2012

(86) PCT No.: PCT/IN2012/000246
§ 371 (c)(1),
(2), (4) Date: Apr. 22, 2013

(87) PCT Pub. No.: WO2012/143937
PCT Pub. Date: Oct. 26, 2012

(65) Prior Publication Data
US 2014/0275538 A1   Sep. 18, 2014

(30) Foreign Application Priority Data
Apr. 15, 2011   (IN) .......................... 1223/MUM/2011

(51) Int. Cl.
*C07D 239/48* (2006.01)
*C07C 253/04* (2006.01)
*C07C 269/06* (2006.01)
*C07C 253/30* (2006.01)

(52) U.S. Cl.
CPC ............ *C07D 239/48* (2013.01); *C07C 269/06* (2013.01); *C07C 253/30* (2013.01); *C07C 253/04* (2013.01)
USPC ......................................... 544/323; 558/403

(58) Field of Classification Search
USPC ......................................... 544/323; 558/403
See application file for complete search history.

(56) References Cited

FOREIGN PATENT DOCUMENTS

IN   2009CH02340   3/2012
WO   WO-2004016581 A1   2/2004

OTHER PUBLICATIONS

International Search Report issued in PCT/IN2012/0000246 on Dec. 13, 2012.

*Primary Examiner* — Kristin Vajda
(74) *Attorney, Agent, or Firm* — Blank Rome LLP

(57) ABSTRACT

Disclosed is process for the preparation of a key Rilpivirine intermediate namely, (E)-4-(2-cyanoethenyl)-2,6-dimethylphenylamine hydrochloride (II) by a process comprising reaction of the tetrafluoroborate salt of the diazonium ion of 2,6-dimethyl-4-amino-1-carboxybenzyl phenylamine (VI) with acrylonitrile in presence of palladium acetate, followed by treatment with an acid and its subsequent conversion to the hydrochloride salt (II), wherein the undesired Z isomer is less than 0.5% and provides Rilpivirine hydrochloride having Z isomer less than 0.1%.

10 Claims, No Drawings

RILPIVIRINE PROCESS

This application is the U.S. national phase of International Application No. PCT/IN2012/000246, filed Apr. 9, 2012, which claims the benefit of Indian Patent Application No. 1223/MUM/2011, filed Apr. 15, 2011.

FIELD OF THE INVENTION

The present invention relates to a novel, cost effective and stereoselective process for the synthesis of Rilpivirine hydrochloride. Typically, the invention relates to a stereoselective synthesis of a key Rilpivirine intermediate namely, (E)-4-(2-cyanoethenyl)-2,6-dimethylphenylamine hydrochloride wherein the desired E isomer is selectively obtained with the undesired Z isomer less than 0.5% and thereby assists in obtaining Rilpivirine hydrochloride having Z-isomer less than 0.1%.

BACKGROUND OF THE INVENTION

Rilpivirine, which is chemically known as 4-{[4-({4-[(1E)-2-cyanoethenyl]-2,6-dimethylphenyl}amino) pyrimidin-2-yl]amino}benzonitrile, is a non-nucleoside reverse transcriptase inhibitor (NNRTI) and exhibits human immunodeficiency virus (HIV) replication inhibiting properties. Rilpivirine is used as its hydrochloride salt in the anti-HIV formulations.

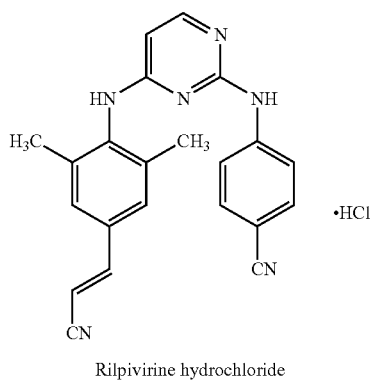

Rilpivirine hydrochloride

Conventionally, various processes followed for the synthesis of Rilpivirine hydrochloride (I), generally involve preparation of the key intermediate, (E)-4-(2-cyanoethenyl)-2,6-dimethylphenylamine hydrochloride of formula (II).

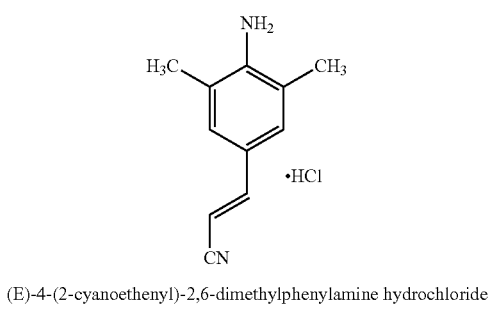

(E)-4-(2-cyanoethenyl)-2,6-dimethylphenylamine hydrochloride

WO 03/016306 first disclosed the synthesis of Rilpivirine involving different routes for synthesis of 4-(2-cyanoethenyl)-2,6-dimethylphenylamine. The first route involved protection of the amino group of 4-bromo-2,6-dimethylphenylamine by converting to N,N-dimethylmethanimidamide, followed by formylation involving n-butyl lithium and dimethylformamide. The resulting formyl derivative was treated with diethyl(cyanomethyl) phosphonate to give the cyanoethenyl compound which was deprotected using zinc chloride to yield the cyanoethenylphenylamine intermediate having an undisclosed E/Z ratio. This route involved an elaborate sequence of synthesis comprising protection of amine by its conversion into imide, use of a highly moisture sensitive and pyrophoric base such as butyl lithium and a low yielding formylation reaction. All these factors made the process highly unviable on industrial scale.

The second route disclosed in WO 03/016306 employed 4-iodo-2,6-dimethylphenylamine as a starting material for synthesis of cyanoethenylphenylamine intermediate, which involved reaction of the dimethylphenylamine derivative with acrylonitrile for at least 12 hours at 130° C. in presence of sodium acetate and a heterogeneous catalyst such as palladium on carbon. Isolation of the desired compound involved solvent treatment with multiple solvents followed by evaporation. This route also does not give any details of the E/Z ratio of the unsaturated intermediate product. Although this route avoids use of phosphine ligands but lengthy reaction time and problem of availability of pure halo-phenylamine derivatives coupled with moderate yields hampers the commercial usefulness of this route.

The third route disclosed in WO 03/016306 involved reaction of 4-bromo-2,6-dimethylphenylamine with acrylamide in presence of palladium acetate, tris(2-methylphenyl)phosphine and N,N-diethylethanamine. The resulting amide was dehydrated using phosphoryl chloride to give 4-(2-cyanoethenyl)-2,6-dimethylphenylamine in a moderate yield of 67% without mentioning the E/Z ratio.

Although the E/Z isomer ratio for the cyanoethenyl derivative obtained from these routes is not specifically disclosed in the patent, however, reproducibility of the abovementioned reactions were found to provide an E/Z ratio between 70/30 and 80/20.

Various other methods have also been reported in the literature for introduction of the cyanoethenyl group in Rilpivirine. The Journal of Medicinal Chemistry (2005), 48, 2072-79 discloses Wittig or Wadsworth-Emmons reaction of the corresponding aldehyde with cyanomethyl triphenylphosphonium chloride to provide a product having an E/Z isomer ratio of 80/20. An alternate method of Heck reaction comprising reaction of aryl bromide with acrylonitrile in presence of tri-o-tolylphosphine and palladium acetate gave the same compound with a higher E/Z isomer ratio of 90/10. The method required further purification in view of the presence of a significant proportion of the Z isomer in the unsaturated intermediate.

A similar method was disclosed in Organic Process Research and Development (2008), 12, 530-536. However, the E/Z ratio of 4-(2-cyanoethenyl)-2,6-dimethylphenylamine was found to be 80/20, which was found to improve to 98/2 (E/Z) after the compound was converted to its hydrochloride salt utilizing ethanol and isopropanol mixture.

It would be evident from the foregoing that prior art methods are associated with the following drawbacks:

a) High proportion of Z isomer, which requires elaborate purification by utilizing column chromatographic techniques, crystallization, or successive treatment with multiple solvents, which decreases the overall yield, b) Introduction of cyanoethenyl group to the formylated benzenamine derivatives involves a moisture sensitive reagent like n-butyl lithium, which is not preferred on industrial scale. Further, the method utilizes cyanomethyl phosphonate esters and is silent about the proportion of the Z isomer and the higher percentage of impurities which requires elaborate purification and ultimately lowers the yield,
c) Prior art routes involve use of phosphine ligands which are expensive, environmentally toxic for large scale operations,
d) Prior art methods utilize phase transfer catalysts such as tetrabutyl ammonium bromide in stoichiometric amounts and the reactions are carried out at very high temperatures of up to 140-150° C.

Thus, there is a need to develop an improved, convenient and cost effective process for preparation of (E)-4-(2-cyanoethenyl)-2,6-dimethylphenylamine hydrochloride of formula (II) having Z-isomer less than 0.5%, without involving any purification and does not involve use of phosphine reagent and which subsequently provides Rilpivirine hydrochloride (I) conforming to regulatory specifications.

The present inventors have developed a process for stereoselective synthesis of the key Rilpivirine intermediate, (E)-4-(2-cyanoethenyl)-2,6-dimethylphenylamine hydrochloride (II), comprising diazotization of 2,6-dimethyl-4-amino-1-carboxybenzyl phenylamine followed by treatment with alkali tetrafluoroborate to provide the tetrafluoroborate salt of the diazonium ion which is followed by reaction with acrylonitrile in presence of palladium (II) acetate and subsequent deprotection of the amino group with an acid followed by treatment with hydrochloric acid to give the desired E isomer of compound (II) having Z isomer content less than 0.5% and with a yield of 75-80%. The compound (II) was subsequently converted to Rilpivirine hydrochloride of formula (I) with Z isomer content less than 0.1%.

OBJECT OF THE INVENTION

An objective of the present invention is to provide (E)-4-(2-cyanoethenyl)-2,6-dimethyl phenylamine hydrochloride (II) having Z isomer less than 0.5% by a convenient, cost-effective, industrially viable process which does not involve use of environmentally toxic phosphine reagents.

Another object of the invention is to provide a process which is amenable for synthesis on a commercial scale and in which the E isomer of 4-(2-cyanoethenyl)-2,6-dimethylphenylamine hydrochloride (II) is selectively synthesized by utilizing reagents which are not hazardous and moisture sensitive.

Yet another object of the present invention is to provide an efficient and cost-effective process for preparation of Rilpivirine hydrochloride (I) with Z-isomer content less than 0.1% by utilizing (E)-4-(2-cyanoethenyl)-2,6-dimethyl phenylamine hydrochloride of formula (II) having undesired Z isomer less than 0.5%.

SUMMARY OF THE INVENTION

The present invention relates to a novel method for synthesis of (E)-4-(2-cyanoethenyl)-2,6-dimethylphenylamine hydrochloride of formula (II) having desired purity.

An aspect of the invention relates to a novel and cost-effective process for preparation of (E)-4-(2-cyanoethenyl)-2,6-dimethylphenylamine hydrochloride (II) having Z-isomer less than 0.5%, by a process comprising reaction of 2,6-dimethyl-4-amino-1-carboxybenzyl phenylamine (V) with sodium nitrite in hydrochloric acid, followed by treatment of the diazotized compound with sodium tetrafluoroborate to give the corresponding tetrafluoroborate salt of formula (VI), which on reaction with acrylonitrile in presence of palladium acetate and a solvent gives compound (VII), which after deprotection with an acid followed by treatment with hydrochloric acid gave compound (II).

Another aspect of the invention relates to a novel and cost-effective process for preparation of Rilpivirine hydrochloride (I) having Z isomer less than 0.1%, comprising reaction of (E)-4-(2-cyanoethenyl)-2,6-dimethylphenylamine hydrochloride of formula (II) with 4-[(4-chloro-2-pyrimidinyl)amino]benzonitrile of formula (XI), in acetonitrile as solvent, isolating Rilpivirine free base at alkaline pH, optionally purifying with acetone, dissolving in dimethyl sulphoxide, heating the mixture to 50-55° C. and adding hydrochloric acid followed by water and isolating Rilpivirine hydrochloride having Z isomer less than 0.1% at a temperature of 25-30° C.

The objectives of the present invention will become more apparent from the following detailed description.

DETAILED DESCRIPTION OF THE INVENTION

The present inventors have surprisingly found that (E)-4-(2-cyanoethenyl)-2,6-dimethylphenylamine hydrochloride (II), having Z isomer less than 0.5% can be prepared in 75-80% yield by the palladium acetate catalyzed reaction of acrylonitrile with diazonium tetrafluoroborate salt of 2,6-dimethyl-4-amino-1-carboxybenzyl phenylamine. Further, Rilpivirine hydrochloride obtained from compound (II) was found to have Z isomer less than 0.1% (Scheme 1).

Scheme 1: Method embodied in the present invention for the preparation of Rilpivirine hydrochloride (I)

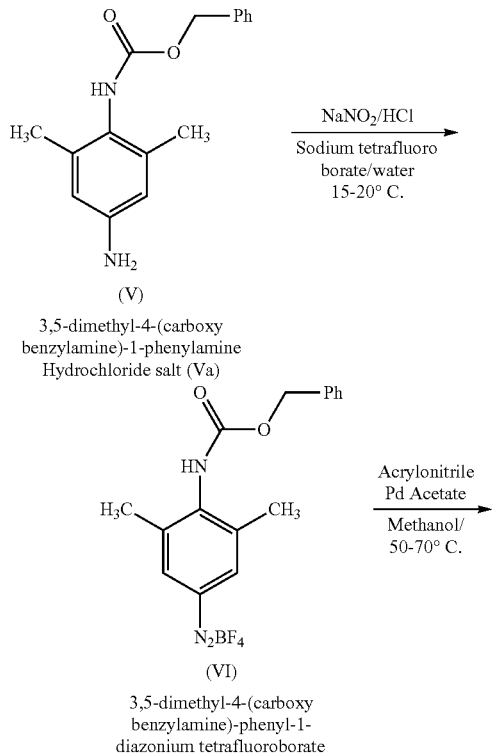

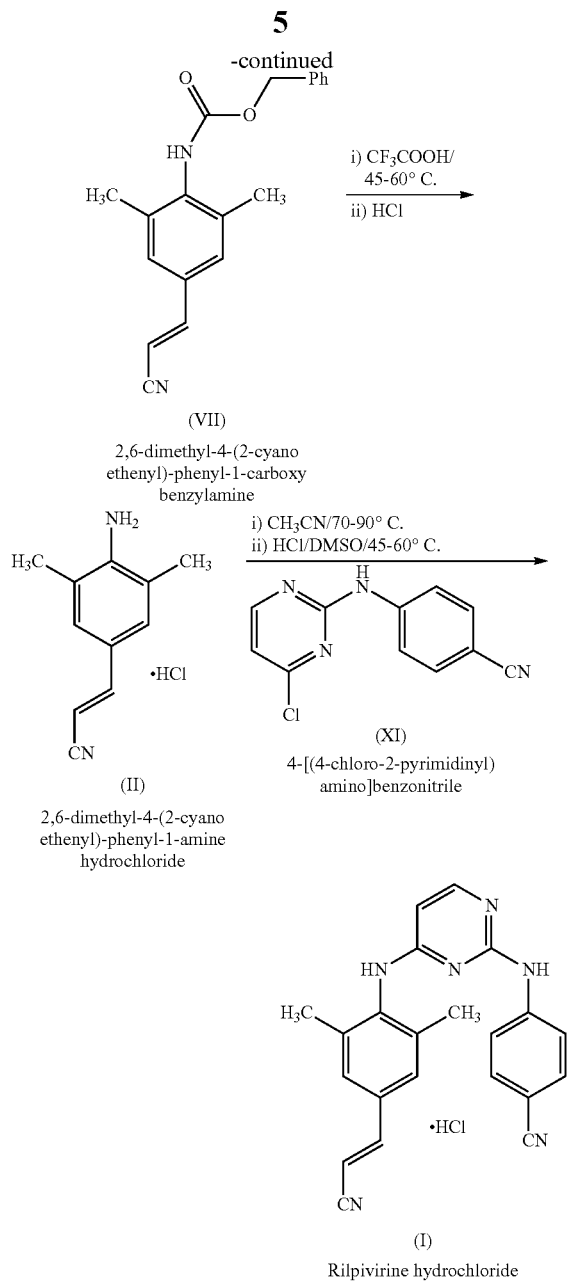

The compound of formula (V) was prepared by reaction of 2,6-dimethyl-4-nitroaniline (III) with benzylchloroformate to give 3,5-dimethyl-4-carboxybenzylamine-1-nitrobenzene (IV), which was then converted to 3,5-dimethyl-4-carboxybenzylamine-1-phenylamine hydrochloride (Va) by reduction with stannous chloride in methanol as solvent.

In an embodiment, 3,5-dimethyl-4-carboxybenzylamine-1-benzeneamine hydrochloride of formula (Va) was treated with sodium nitrite in presence of hydrochloric acid in an aqueous medium at 0 to 25° C. to give the diazonium compound. After completion of the reaction as monitored by HPLC, the reaction mixture was treated with aqueous tetrafluoroborate solution to yield 3,5-dimethyl-4-carboxybenzylamino-1-diazonium tetrafluoroborate (VI).

The aqueous tetrafluoroborate solution was prepared by dissolving an alkali tetrafluoroborate such as sodium tetrafluoroborate or potassium tetrafluoroborate in water to obtain a 30-50% aqueous solution.

The arenediazonium tetrafluoroborate salt of formula (VI), which separated out was filtered and dried. An organic solvent was added to the compound of formula (V).

The organic solvent was selected from the group comprising of ethanol, methanol, isopropanol, dimethyl formamide, dimethyl acetamide and tetrahydrofuran.

Acrylonitrile was gradually added to the mixture in presence of palladium acetate and stirred at ambient temperature till completion of reaction. The reaction mass was filtered and concentrated to provide a residue containing 2,6-dimethyl-4-(2-cyanoethenyl)-1-carboxybenzyl phenylamine (VII).

An organic or inorganic acid but preferably an organic acid such as trifluoroacetic acid was employed for deprotection of compound (VII).

Trifluoroacetic acid was added to the residue and stirred at 40-60° C. till completion of reaction as monitored by TLC. The reaction mass was quenched with water and neutralized with liquid ammonia. The mixture was extracted with a water-immiscible solvent like toluene. The organic layer was concentrated and treated with a mixture of an alcohol like isopropanol and ether like diisopropyl ether. Hydrochloric acid dissolved in isopropanol was then added to the mixture to separate out (E)-4-(2-cyanoethenyl)-2,6-dimethylphenylamine hydrochloride (II).

It is pertinent to note that compound (II) was obtained with a yield of 75-80% and was found to have Z isomer less than 0.5% which was easily reduced to below 0.1% in Rilpivirine hydrochloride.

This is in stark contrast to prior art methods wherein (E)-4-(2-cyanoethenyl)-2,6-dimethylphenylamine hydrochloride (II) is isolated with Z isomer more than 2% and requires repeated purification for obtaining Z isomer below the desired limits in Rilpivirine hydrochloride (I).

(E)-4-(2-Cyanoethenyl)-2,6-dimethylphenylamine hydrochloride (II) was then dissolved in acetonitrile and after addition of 4-[(4-chloro-2-pyrimidinyl)amino]benzonitrile (XI), the resulting mixture was heated at 70 to 90° C. till completion of reaction as monitored by HPLC. The reaction mixture was then cooled to 40° C. and Rilpivirine base started to separate out when the reaction mixture was made alkaline with an aqueous solution of an inorganic base like sodium carbonate.

Rilpivirine free base was then purified by refluxing in an organic solvent like acetone and after optional carbon treatment was partially concentrated, cooled and filtered.

The wet cake having Z-isomer ≈0.6% was dried, dissolved in dimethyl sulphoxide, and after mixing gradually with hydrochloric acid at 50-55° C. was diluted with water at same temperature.

The final product, which had separated out was filtered at 25 to 30° C. and washed with water to provide Rilpivirine hydrochloride having Z-isomer less than 0.1%. It was observed that the filtration temperature was critical for obtaining the finished product with Z isomer content less than 0.1%.

The inventors found that no further purification was required thereby obviating any chance of loss in yield.

The compound of formula (XI) required for preparation of rilpivirine free base was obtained as disclosed in Scheme-2.

Scheme 2: Preparation of 4-[(4-chloro-2-pyrimidinyl)amino]benzonitrile (XI)

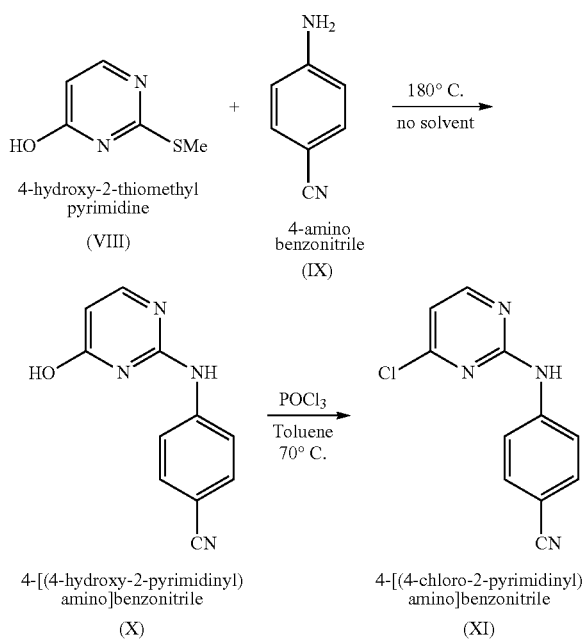

4-Hydroxy-2-thiomethylpyrimidine of formula (VIII) was treated with 4-aminobenzonitrile of formula (IX) in the temperature range of 170 to 190° C. and in absence of a solvent to provide 4-[(4-hydroxy-2-pyrimidinyl)amino]benzonitrile of formula (X) of desired purity.

Compound (X) was further treated with phosphorous oxychloride to yield 4-[(4-chloro-2-pyrimidinyl)amino]benzonitrile of formula (XI). The reaction was carried out in the temperature range of 60 to 80° C., using toluene as a solvent.

The following examples are meant to be illustrative of the present invention. These examples exemplify the invention and are not to be construed as limiting the scope of the invention.

EXAMPLES

Example 1

Synthesis of 3,5-dimethyl-4-carboxybenzylamine-phenyl-1-diazonium tetrafluoroborate (VI)

3,5-Dimethyl-4-carboxybenzylamine-1-phenylamine hydrochloride (150 gms) was added to water (1500 ml) and the reaction mixture was cooled to 10 to 15° C. Concentrated hydrochloric acid (150 ml) was slowly added to the reaction mass, followed by addition of 50% aqueous sodium nitrite solution (102 ml) and stirred at same temperature. After completion of the reaction as monitored by TLC, a 50% aqueous solution of sodium tetrafluoroborate (323 ml) was added to the reaction mass and stirred. The tetrafluoroborate salt separating out from the reaction mass was filtered and dried to yield 3,5-dimethyl-4-carboxybenzylamine-phenyl-1-diazonium tetrafluoroborate.

Yield=165 gms
% Yield: 91%

Example 2

Synthesis of 2,6-dimethyl-4-(2-cyanoethenyl)-1-carboxybenzyl phenylamine (VII)

Acrylonitrile (43.1 gms) was gradually added to 3,5-dimethyl-4-carboxybenzylamine-phenyl-1-diazonium tetrafluoroborate (200 gms) in methanol (2000 ml). Palladium acetate (5 gms) was added to the reaction mass under stirring at 25 to 30° C. and the reaction mass was stirred till completion of the reaction. Upon completion, the reaction mass was filtered, and concentrated to give a residue containing 2,6-dimethyl-4-(2-cyanoethenyl)-1-carboxybenzylphenylamine (VII) which was utilized for next reaction.

Yield=161 gms

Example 3

Synthesis of 2,6-dimethyl-4-(2-cyanoethenyl)phenylamine hydrochloride (II)

Trifluoroacetic acid (600 ml) was slowly added to the residue of 2,6-dimethyl-4-(2-cyanoethenyl)-1-carboxybenzyl phenylamine obtained from example 2 (161 gms) at 25 to 30° C. and the reaction mass was stirred at 45-60° C. till completion of reaction as monitored by TLC. After completion of the reaction, water (1800 ml) was added to the reaction mass, neutralized with aqueous ammonia and extracted with toluene. The organic layer was separated and concentrated to give 2,6-dimethyl-4-(2-cyanoethenyl)phenylamine. The residue was admixed with 1:1 mixture of isopropanol and diisopropyl ether (1000 ml) and treated with HCl dissolved in isopropanol to yield 2,6-dimethyl-4-(2-cyanoethenyl)phenylamine hydrochloride salt (II) which was cooled to 25-30° C., filtered and dried.

Yield=90 g
% Yield: 80% (based on compound VI)

Example 4

Synthesis of 3,5-dimethyl-4-carboxybenzylamine-1-nitrobenzene (IV)

A solution of benzylchloroformate (1027 gms; 50% solution in toluene) was slowly added to a suspension of 2,6-dimethyl-4-nitroaniline (100 gms) in toluene (1000 ml) at 25 to 30° C. The mixture was refluxed till completion of the reaction. The reaction mixture was cooled at 10-15° C., filtered and dried to give 3,5-dimethyl-4-carboxybenzylamine-1-nitrobenzene (IV).

Yield: 160 g
% Yield: 88%

Example 5

Synthesis of 3,5-dimethyl-4-carboxybenzylamine-1-phenylamine hydrochloride (Va)

Stannous chloride dihydrate (394 gms) was added to a mixture of 3,5-dimethyl-4-carboxybenzylamine-1-nitrobenzene (150 gms) and methanol (1500 ml). The reaction mass was heated at 60 to 65° C. and stirred till completion of reaction, as monitored by HPLC. The reaction mixture was concentrated and the residue was diluted with water (750 ml).

A 20% solution of sodium hydroxide (2000 ml) was added slowly with stirring at 15 to 20° C. The mixture was extracted with dichloromethane and the organic layer was stirred with hydrochloric acid at 10-15° C. to separate 3,5-dimethyl-4-carboxybenzylamine-1-phenylamine hydrochloride salt (Va), which was filtered and dried.

Yield=145 gms
% Yield: 94%

Example 6

Synthesis of 4-[(4-chloro-2-pyrimidinyl)amino]benzonitrile (X)

A mixture of 4-hydroxy-2-thiomethylpyrimidine (VIII) (500 gms) and 4-aminobenzonitrile (IX; 1246.5 g) was heated slowly to 100 to 125° C., with stirring, followed by further heating at 180 to 185° C. which was continued till the reaction was complete, as monitored by HPLC. The reaction mass was then cooled to 100-110° C. and toluene (2000 ml) was added to it. The reaction mass was stirred at 100 to 110° C., cooled to ambient temperature, filtered and dried to give 4-[(4-hydroxy-2-pyrimidinyl)amino]benzonitrile. Toluene (2500 ml) was added to it and phosphorus oxychloride (434.5 gms) was slowly added to the mixture at 50 to 70° C. The reaction mass was stirred at 70 to 75° C. till completion of reaction and cooled to 10-20° C., quenched with water and neutralized by adding sodium carbonate solution, filtered at 10-20° C. and dried to give 4-[(4-chloro-2-pyrimidinyl)amino]benzonitrile (X).

Yield=450 g
% Yield: 83%

Example 7

Synthesis of Rilpivirine hydrochloride

4-[(4-chloro-2-pyrimidinyl)amino]benzonitrile (100 gms) and 2,6-dimethyl-4-(2-cyanoethenyl) phenylamine hydrochloride (90.65 gms) were mixed with acetonitrile (800 ml) in an inert atmosphere and heated at 85-90° C. till completion of the reaction, as monitored by HPLC. The reaction mixture was cooled to 40° C. and pH of the reaction mass was adjusted to ≈pH 10 with 20% sodium carbonate solution. The reaction mass was filtered at 5 to 10° C. and dried to yield Rilpivirine (110 gms). Rilpivirine thus obtained was dissolved in acetone (3600 ml) and after optional charcoal treatment was concentrated to 500 ml and was filtered at 5-10° C., dried to give Rilpivirine (80 gms), which was then added to dimethyl sulfoxide (338 ml) and heated to 70-75° C. The mixture was cooled to 50 to 55° C. and mixed with hydrochloric acid (25 ml) with constant stirring. Water (1350 ml) was added to the mixture at 40 to 45° C., which was stirred and cooled further. The reaction mass was filtered at 25 to 30° C. and the wet cake was dried to give 90 gms of Rilpivirine hydrochloride (I) having Z isomer less than 0.1%.

We claim:

1. A process for the preparation of (E)-4-(2-cyanoethenyl)-2,6-dimethylphenylamine hydrochloride comprising
    (a) reacting 2,6-dimethyl-4-amino-l-carboxybenzyl phenyl amine with sodium nitrite in hydrochloric acid to form a diazotized compound,
    (b) reacting the diazotized compound with an alkali tetrafluoroborate to give the corresponding tetrafluoroborate salt,
    (c) reacting the tetrafluoroborate salt with acrylonitrile in presence of palladium acetate and a solvent to form 2,6-dimethyl-4-(2-cyanoethyl)-phenyl-1-carboxy benzylamine,
    (d) deprotecting the 2,6-dimethyl-4-(2-cyanoethyl)-phenyl-1-carboxy benzylamine with an acid, and
    (e) treating the product of step (d) with hydrochloric acid to afford (E)-4-(2-cyanoethenyl)-2,6-dimethylphenylamine hydrochloride,
    wherein the (E)-4-(2-cyanoethenyl)-2,6-dimethylphenylamine hydrochloride contains less than 0.5% of the Z-isomer.

2. The process of claim 1, wherein the solvent in step (c) is selected from methanol, ethanol, isopropanol, dimethyl formamide, dimethyl acetamide and tetrahydrofuran.

3. The process of claim 1, wherein the deprotection in step (d) is performed by adding an organic acid.

4. The process of claim 3, wherein the organic acid is trifluoroacetic acid.

5. The process of claim 2, wherein the alkali tetrafluoroborate is selected from sodium tetrafluoroborate and potassium tetrafluoroborate.

6. A process for preparation of rilpivirine hydrochloride containing less than 0.1% of the Z-isomer, comprising
    (a) reacting (E)-4-(2-cyanoethenyl)-2,6-dimethylphenylamine hydrochloride containing less than 0.5% of the Z-isomer with 4-[(4-chloro-2-pyrimidinyl)aminol]benzonitrile in acetonitrile,
    (b) isolating rilpivirine free base at alkaline pH,
    (c) optionally purifying the rilpivirine free base with acetone,
    (d) dissolving the rilpivirine free base in dimethyl sulphoxide,
    (e) heating the mixture of step (d) to 50-55° C.,
    (f) adding hydrochloric acid followed by water, and
    (g) isolating the rilpivirine hydrochloride at a temperature of 25-30° C.

7. The process of claim 1, wherein the 2,6-dimethyl-4-amino-l-carboxybenzyl phenyl amine is prepared by a process comprising reacting 2,6-dimethyl-4-nitroaniline (III) with benzyl chloroformate, and treating the resulting product with stannous chloride.

8. (E)-4-(2-cyanoethenyl)-2,6-dimethylphenylamine hydrochloride containing less than 0.5% of the Z-isomer.

9. A method of preparing rilpivirine hydrochloride comprising
    (a) reacting the (E)-4-(2-cyanoethenyl)-2,6-dimethylphenylamine hydrochloride of claim 8 with 4-[(4-chloro-2-pyrimidinyl)aminol ]benzonitrile to afford rilpivirine free base, and
    adding hydrochloric acid to the rilpivirine free base to afford rilvipirine hydrochloride.

10. The process of claim 1, further comprising converting the (E)-4-(2-cyanoethenyl)-2,6-dimethylphenylamine hydrochloride to rilpivirine hydrochloride.

* * * * *